United States Patent [19]
Gamblin et al.

[11] Patent Number: 6,156,701
[45] Date of Patent: Dec. 5, 2000

[54] HERBICIDAL METHOD

[75] Inventors: Alan Gamblin; Ashley Slater, both of Ongar, United Kingdom

[73] Assignee: Rhone-Poulenc Agro, Lyons, France

[21] Appl. No.: 09/380,747

[22] PCT Filed: Mar. 11, 1998

[86] PCT No.: PCT/EP98/01397

§ 371 Date: Nov. 24, 1998

§ 102(e) Date: Nov. 24, 1998

[87] PCT Pub. No.: WO98/39971

PCT Pub. Date: Sep. 17, 1998

[30] Foreign Application Priority Data

Mar. 12, 1997 [GB] United Kingdom ............... 9705039

[51] Int. Cl.[7] .................................................. A01N 43/80
[52] U.S. Cl. ............................................................. 504/271
[58] Field of Search ............................................. 504/271

[56] References Cited

U.S. PATENT DOCUMENTS 5,656,573  8/1997  Roberts et al. .................. 504/271
5,837,652  11/1998  Anderson-Taylor et al. ....... 504/138

FOREIGN PATENT DOCUMENTS 0487357  5/1992  European Pat. Off. .
0527036  2/1993  European Pat. Off. .
97/22253  6/1997  WIPO .

OTHER PUBLICATIONS

Luscombe et al., *Proc. Br. Crop. Prot. Conf. Weeds*, vol. 1, pp. 35–42 (1995).

CAB International, CAB Accession No. 972303038 (1997), abstract of Bhowmik et al, Proceedings of the Second International Weed Control Congress, Copenhagen, Denmark, Jun. 25–28, 1996, vol. 1–4, pp. 807–812. (Abstract Only).

*Primary Examiner*—S. Mark Clardy
*Assistant Examiner*—Alton Pryor
*Attorney, Agent, or Firm*—Burns, Doane, Swecker & Mathis, L.L.P.

[57] ABSTRACT

This invention is directed to a method of selectively controlling undesirable vegetation in corn, comprising application of an herbicidally effective amount of an isoxazole having the formula

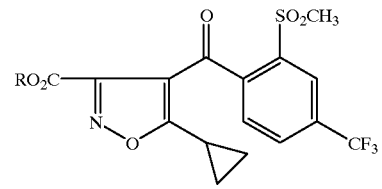

wherein R is a straight- or branched-chain alkyl having up to six carbon atoms, to the locus of such vegetation.

3 Claims, No Drawings

HERBICIDAL METHOD

This application is a 371 of PCT/EP98/01397 filed Mar. 11, 1998.

FIELD OF THE INVENTION

The present invention is directed to the use of 3-ester-4-benzoylisoxazoles as a selective pre-emergence and post-emergence herbicide in corn.

BACKGROUND OF THE INVENTION

The protection of crops from weeds and other vegetation which inhibit crop growth is a constantly recurring problem in agriculture. To help combat this problem researchers in the field of synthetic chemistry have produced an extensive variety of chemicals and chemical formulations effective in the control of such unwanted growth. Chemical herbicides of many types have been disclosed in the literature and a large number are in commercial use.

Unfortunately, many of such herbicides will exhibit phototoxicity to the desired crop as well as to the weeds sought to be controlled. Thus, there is a long-standing need for selective herbicides which will not adversely affect the crop plants when applied at herbicidally effective levels.

Isoxaflutole [5-cyclopropyl-4-(2-methylsulfonyl-4-trifluoromethyl)benzoylisoxazole] is disclosed in European Patent Publication No. EP-0527036 and is a highly effective herbicide in corn. used pre-emergence or pre-plant incorporated [see for example Vrabel et al., Proc. North Cent. Weed Sci. Soc. Volume 49. pages 49–50 (1994); and Luscombe et al. Proc. Br. Crop Prot. Conf. Weeds. Volume 1. pages 35–42 (1995)]. At elevated dose rates however, or when applied post-emergence a problem can exist that corn may be damaged by this compound. European Patent Publication No. EP-0487357 describes. interalia. 3-ester-4-benzoylisoxazoles having activity against a variety of weed species. In particular, EP-0487357 describes ethyl 5-cyclopropyl-4-(2-methylsulfonyl-4-trifluoromethyl)benzoylisoxazole-3-carboxylate (as Compound BB).

It has now been discovered that such compounds will effectively control a broad range of weeds typically associated with corn without exhibiting any substantial phytotoxic effects on the corn itself.

DESCRIPTION OF THE INVENTION

This invention is directed to a method of selectively controlling undesirable vegetation in corn, comprising application of an herbicidally effective amount of an isoxazole having the formula (I):

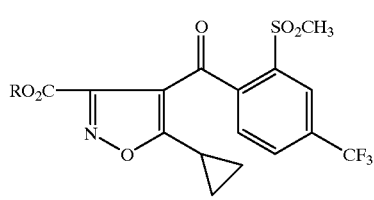

(I)

wherein R is a straight- or branched-$C_{1-6}$ alkyl, to the locus of such vegetation.

As is employed herein, the term "herbicide" is used to denote a compound which controls or modifies the growth of plants. The term "herbicidally effective amount" is used to indicate the quantity of such compound which is capable of producing a controlling or modifying effect. Controlling or modifying effects include all deviations from natural development, for example: killing, retardation, leaf burn, albinism, dwarfing, and the like. The term "plants" refers to all physical parts of a plant including seeds, seedlings, saplings, roots, tubers, stems, stalks, foliage and fruits. Preferably R is straight- or branched $C_{1-3}$ alkyl. Most preferably R is ethyl, i.e. ethyl 5-cyclopropyl-4-(2-methylsulfonyl-4-trifluoromethyl)benzoylisoxazole-3-carboxylate, which is hereafter referred to as Compound A. Compounds of formula (I) above are known from EP-0487357 or can be prepared by the methods described in that publication.

In the practice of the present invention isoxazole is applied to the locus of the vegetation to be controlled. Application rates will depend on the particular plant species and degree of control desired. In general, application rates of from about 10 to about 250 g/ha may be employed, with rates of from about 50 to about 200 g/ha being preferred, and from about 50 to about 150 g/ha more preferred, about 75 to about 150 g/ha even more preferred.

The compound of formula (I) can be formulated in the same manner in which herbicides are generally formulated. The object of the formulation is to apply the compositions to the locus where control is desired by a convenient method. The "locus" is intended to include soil, as well as established vegetation.

The method can be used by pre- or post-emergence application.

By the term 'pre-emergence application' is meant application to the soil in which the weed seeds or seedlings are present before emergence of the crop. One example of a pre-emergence application is known as 'pre-plant incorporated' (PPI), where the herbicide is incorporated into the soil before planting the crop. Another is where the herbicide is applied to the soil surface after sowing the crop. By the term 'post-emergence application' is meant application to the aerial or exposed portions of the weeds which have emerged above the surface of the soil.

In practice, the isoxazole is generally applied as a formulation containing various adjuvants and carriers known to or used in the industry for facilitating dispersion. The choice of formulation and mode of application for isoxazole may affect its activity, and selection will be made accordingly. The isoxazole may thus be formulated as wettable powders, as flowable formulations, as emulsions, as granular formulations, as water dispersible granules, as powders or dusts. These formulations may contain as little as about 0.5% to as much as about 95% or more by weight of isoxazole. The optimum amount in any particular formulation will depend upon the materials in the formulation and the type of seeds or plants to be controlled.

Wettable powders (WP) are in the form of finely divided particles which disperse readily in water or other liquid carriers. The particles contain the active ingredient retained in a solid matrix. Typical solid matrices include fuller's earth, kaolin clays, silicas, and other readily wet organic or inorganic solids. Wettable powders normally contain about 5% to about 95% of the active ingredient plus a small amount of wetting, dispersing, or emulsifying agent.

Flowable formulations, also known as Suspension Concentrates (SC), are stable suspension of active ingredient(s) intended for dissolution before use. This type of formulation consists of a dispersion of finely divide active ingredient(s) which may be practically insoluble or only slightly soluble in water or in organic solvents chosen as the diluent. It also contains inert materials such as dispersants, wetting agents, suspending aids and diluent. In general, flowable formulations tend to be creamy in appearance and readily mixable with water.

Emulsions, also known as emulsifiable concentrates (EC), are heterogeneous dispersions of one liquid in another liquid with which it is incompletely miscible. There are two common types, a dispersion of fine globules of an organic liquid in water (O/W type), and, less commonly, a dispersion of globules of an aqueous liquid in oil (W/O type). A stable mixture is produced by the addition of appropriate emulsifying agents. Typically, this type of formulation will contain 1 to 90% active ingredient.

Granular formulations, generally referred to as Impregnated Granular Formulations (GR) contain active ingredients impregnated in carriers. Inert materials of granular formulations include extrudates. relatively coarse particles ("carriers"), and surface active agents. Typical carriers of granular formulations include: sand, fuller's earth, vermiculite, perlite, and other organic or inorganic materials which can be coated with the active compound. Typical surface active agents are: 1) heavy aromatic naphthas, kerosene and other petroleum fractions, 2) vegetable oils, and 3) stickers, such as dextrins, glue, or synthetic resins. Granular formulations are usually applied to weeds without being diluted.

Water Dispersible Granules (WG or WDG) formulations consist of small granules to be disintegrated and dispersed in water prior to application. Granules can be formed either by agglomeration or through the use of elevated pressure, for example, extrusion. Surface active agents, such as dispersants and wetting agents, are essential ingredients of the formulation. Clays, silicas and starch, among others, can be used as carriers. Powders or dusts are free-flowing admixtures of the active ingredient with finely divided solids such as talc, clays, flours, and other organic and inorganic solids which act as dispersants and carriers.

Other useful formulations for herbicidal applications include simple solutions, sometimes described as flowable formulations, of the active ingredient in a solvent in which it is completely soluble at the desired concentration, such as water, acetone, alkylated naphthalenes. xylene, and other organic solvents. Pressurized sprayers, wherein the active ingredient is dispersed in finely-divided form as a result of vaporization of a low boiling dispersant solvent carrier, may also be used.

Many of these formulations include wetting, dispersing or emulsifying agents. Examples of these agents are alkyl and alkylaryl sulfonates and sulfates and their salts, polyhydric alcohols. polyethoxylated alcohols, esters and fart) amines. These agents, when used, normally comprise from 0.1% to 15% by weight of the formulation.

Each of the above formulations can be prepared as a package containing the herbicide together with other ingredients of the formulation (diluents, emulsifiers, surfactants etc.). The formulation can also be prepared by a tank mix method in which the ingredients are obtained separately and combined at the grower site.

These formulations can be applied by conventional methods to the areas where control is desired. Dust and liquid compositions, for example, can be applied by the use of power dusters, boom and hand sprayers, and spray dusters. The formulations can also be applied from airplanes as a dust or a spray or by rope wick applications. To modify or control growth of germinating sees or emerging seedlings, dust and liquid formulations can be distributed in the soil to a depth of at least one centimeter below the soil surface or can be applied to the soil surface only, by spraying or sprinkling. The formulations can also be applied by addition to irrigation water, permitting penetration of the formulations into the soil together with the irrigation water. Dust compositions, granular compositions, or liquid formulations applied to the surface of the soil can be distributed below the surface of the soil by conventional means such as discing or mixing operations.

The following Example is intended to illustrate the invention and is not in any way intended to limit the scope of this invention.

EXAMPLE

The following Example demonstrates the properties of a representative compound of the invention, ethyl 5-cyclopropyl-4-(2-methylsulfonyl-4-trifluoromethyl) benzoylisoxazole-3-carboxylate, referred to as Compound A.

Example 1

A series of replicated small plot field experiments were carried out in April to July post-emergence of the crop and weed species in the United States (Nebraska and North Carolina), Spain and Italy. The crop (corn, *Zea mais*) and the weeds were drilled using standard or modified farm equipment. Weeds drilled were those commonly occurring in maize crops. Test areas were spray irrigated as required to ensure adequate plant growth. Plot layout was a randomised block with 3 replicates (2 in the case of Spain ). Individual plot sizes were between 6.95 and 15.0 square meters. The test compounds were formulated as wettable powders diluted with water and applied with a pneumatic sprayer. The spray pressure was 1.4–2.0 Bar and the volume rate was 187–500 l/ha. Assessment of crop responses and weed control were carried out at intervals post application by visual assessment of percentage effect in individual replicates on individual species. For weed control 100 percent means complete control and for crop phytotoxicity 100 percent means complete crop destruction. A mean of the replicates was calculated. In the Tables that follow 'DAT' means the Days after treatment/application of the test compound; 'AI' means active ingredient; 'AMAR' is the weed species *Amaranthus retroflexus*. 'ABUT' is *Abutilon theophrasti*; 'SETVI' is *Setaria viridis*. Compound A was compared with the prior art compound isoxaflutole, 5-cyclopropyl-4-(2-methylsulfonyl-4-trifluoromethyl) benzoylisoxazole. which differs from Compound A in not having 3-ethyl ester grouping. This is referred to in the Table as the "Prior Art".

| Results | | | | | |
|---|---|---|---|---|---|
| Mean corn (*Zea mais*) phototoxicity score from visual assessment | | | | | |
| Treatment | Dose g AI/ha | USA Nebraska | USA N.Carolina | Spain Seville | Italy Bologna |
| Compound A | 50 | 0 | 0 | 5 | 3.7 |
| Compound A | 100 | 0 | 0 | 5 | 3.5 |
| Compound A | 150 | 0 | 3.3 | 5 | 2.5 |
|  | Assessment timing Maize variety | 7 DAT Pioneer 3162 | 7 DAT Pioneer 3320 | 8 DAT Juanita | 10 DAT No data |
| Prior Art | 50 | 2.3 | 6.7 | 15 | 14 |
| Prior Art | 100 | 9 | 22 | 20 | 23 |
| Prior Art | 150 | 3.3 | 23.3 | 22.5 | 27.5 |

| Mean weed control from visual assessment of 3 replicates | | | | | | | |
|---|---|---|---|---|---|---|---|
|  | Dose g | USA Nebraska | | | USA N. Carolina | | |
| Treatment | AI/ha | AMAR | ABUT | SETVI | AMAR | ABUT | SETVI |
| Compound A | 100 | 100 | 100 | 77 | 70 | 100 | 71 |
| Compound A | 150 | 100 | 100 | 80 | 67 | 100 | 75 |
| Prior Art | 100 | 100 | 80 | 82 | 86 | 100 | 83 |
| Prior Art | 150 | 100 | 92 | 88 | 99 | 100 | 85 |

| Mean weed control from visual assessment of 3 replicates | | | | | | |
|---|---|---|---|---|---|---|
|  | Dose g | Spain Seville | | | Italy Bologna | |
| Treatment | AI/ha | AMAR | ABUT | SETVI | AMAR | SETVI |
| Compound A | 100 | 99 | 70 | 75 | 85 | 100 |
| Compound A | 150 | 100 | 80 | 75 | 75 | 100 |
| Prior Art | 100 | 99 | 77 | 77 | 91 | 95 |
| Prior Art | 150 | 100 | 85 | 75 | 96 | 100 |

The results above show that Compound A gives rise to low crop phytotoxicity whilst maintaining a commercially acceptable level of weed control, and possesses a superior margin of crop selectivity in comparison with the prior art compound, isoxaflutole.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for selectively controlling undesired vegetation comprising *Amaranthus retroflexus, Abutilon theophrasti* or *Setaria viridis* post-emergence in corn, said method comprising applying a herbicidally effective amount of ethyl 5-cyclopropyl-4-(2-methylsulfonyl-4-trifluoromethyl)benzoylisoxazole-3-carboxylate to the locus of said vegetation, post-emergence of the corn, said herbicidally effective amount being an amount which has no or low phytotoxicity to corn, said herbicidally effective amount being from about 50 to about 250 g/ha and being sufficient to destroy an average of at least 80% of the *Amaranthus retroflexus, Abutilon theophrasti* or *Setaria viridis*.

2. A method according to claim 1, wherein said herbicidally effective amount is from about 75 to about 150 g/ha.

3. A method according to claim 2, wherein said herbicidally effective amount is from about 100 to about 150 g/ha.

* * * * *